(12) United States Patent
Oberdoerfer et al.

(10) Patent No.: US 8,770,027 B2
(45) Date of Patent: *Jul. 8, 2014

(54) PULSE-ECHO METHOD BY MEANS OF AN ARRAY-TYPE PROBE AND TEMPERATURE COMPENSATION

(75) Inventors: York Oberdoerfer, Langenfeld (DE); Michael Berke, Cologne (DE); Wolf-Dietrich Kleinert, Bonn (DE); Jerome Poirier, Saulx les Chatreux (FR); Sascha Schieke, Greer, SC (US)

(73) Assignee: GE Sensing & Inspection Technologies GmbH (DE)

( * ) Notice: Subject to any disclaimer, the term of this patent is extended or adjusted under 35 U.S.C. 154(b) by 490 days.

This patent is subject to a terminal disclaimer.

(21) Appl. No.: 13/062,032

(22) PCT Filed: Sep. 7, 2009

(86) PCT No.: PCT/EP2009/061581
§ 371 (c)(1),
(2), (4) Date: Jun. 22, 2011

(87) PCT Pub. No.: WO2010/026253
PCT Pub. Date: Mar. 11, 2010

(65) Prior Publication Data
US 2011/0247417 A1    Oct. 13, 2011

(30) Foreign Application Priority Data
Sep. 5, 2008 (DE) .................. 10 2008 041 835

(51) Int. Cl.
*G01N 29/07* (2006.01)
*G01N 29/32* (2006.01)

(52) U.S. Cl.
USPC ................................ 73/597; 73/598; 73/627

(58) Field of Classification Search
USPC ........... 73/597, 598, 614–616, 609, 602, 627, 73/628
See application file for complete search history.

(56) References Cited

U.S. PATENT DOCUMENTS 4,182,155 A * 1/1980 Fowler ........................... 73/1.81
4,398,421 A * 8/1983 White ............................. 73/597

(Continued)

FOREIGN PATENT DOCUMENTS

DE        3327526        4/1984
DE        3441894        7/1986

(Continued)

OTHER PUBLICATIONS

International Search Report; PCT/EP2009/061581; Nov. 20, 2009.

(Continued)

Primary Examiner — Helen Kwok
(74) Attorney, Agent, or Firm — Cantor Colburn LLP

(57) ABSTRACT

The invention relates to a nondestructive ultrasonic test method in which at least one ultrasonic pulse is emitted into a workpiece under test by at least one ultrasonic transmitter (3), the ultrasonic pulse is reflected on boundary surfaces within the workpiece, the reflected ultrasound is received by at least one ultrasonic receiver (2), and the associated signals are evaluated, the ultrasound penetrating a damping block (4) that is arranged between the workpiece and the transmitter or receiver. The method is characterized in that it includes at least one step for determining at least one dimension (alpha, $d_1$, $d_2$) of the damping block (4) that is relevant for the ultrasonic test; in said step, the propagation time of at least one ultrasonic pulse which is generated by the ultrasonic transmitter (3), is reflected on a boundary surface (5) of the damping block (4), and is received by the ultrasonic receiver (2) is measured, and at least one dimension (alpha, $d_1$, $d_2$) of the damping block (4) that is relevant for the ultrasonic test is determined from the measurement.

11 Claims, 1 Drawing Sheet

(56) References Cited

U.S. PATENT DOCUMENTS

| | | | |
|---|---|---|---|
| 4,413,517 A * | 11/1983 | Soden | 73/597 |
| 4,437,332 A * | 3/1984 | Pittaro | 73/597 |
| 4,680,967 A * | 7/1987 | Rost | 73/628 |
| 5,201,225 A * | 4/1993 | Takahashi et al. | 73/615 |
| 6,082,180 A | 7/2000 | Greenwood | |
| 7,194,907 B2 * | 3/2007 | Abbate et al. | 73/597 |
| 7,415,880 B2 * | 8/2008 | Renzel | 73/597 |
| 8,150,652 B2 * | 4/2012 | Rager et al. | 702/159 |
| 8,156,784 B2 * | 4/2012 | DeAngelo et al. | 73/1.82 |
| 8,210,046 B2 * | 7/2012 | Luo et al. | 73/644 |
| 2008/0127732 A1 | 6/2008 | Owens et al. | |
| 2011/0239768 A1 * | 10/2011 | Berke et al. | 73/627 |

FOREIGN PATENT DOCUMENTS

| | | |
|---|---|---|
| DE | 10112583 | 10/2002 |
| WO | 2007/144271 | 12/2007 |

OTHER PUBLICATIONS

Song S-J et al: "Simulation of 3-D radiation beam patterns propagated through a planar interface from ultrasonic phased array transducers"; Ultrasonics, IPC Science and Technology, vol. 40, No. 1-8, May 1, 2002, pp. 519-524; XP004357251.

* cited by examiner

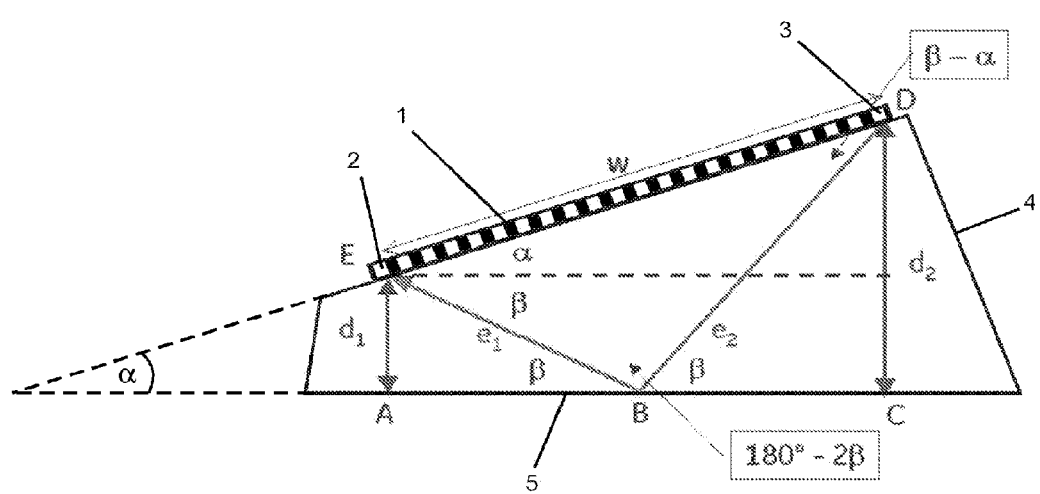

PULSE-ECHO METHOD BY MEANS OF AN ARRAY-TYPE PROBE AND TEMPERATURE COMPENSATION

TECHNICAL FIELD

The invention relates to a pulse-echo method for ultrasound material inspection and a device therefor. This is an acoustic method for finding material flaws in which ultrasound is used. Ultrasound testing belongs to the non-destructive testing methods. In this manner, components can be inspected also in the fitted state, e.g. the supporting members of an airplane. Ultrasound testing is a suitable testing method for finding internal and external flaws in sound-conducting materials (to which most metals belong), for example in welding seams, forgings, cast, semi-finished products or pipes. In mechanical engineering, quality control of components is an important task in order to ensure, for example, the safety of passenger transport devices or of pipelines, for example for hazardous substances. Laid railroad tracks are routinely inspected by test trains. Therefore, the enhancement of the reliability and accuracy of these methods is intended.

BACKGROUND

Like all testing methods, ultrasound inspection is also standardized and is carried out in accordance with guidelines, such as according to DIN EN 10228-3 1998-07 Zerstörungsfreie Prüfung von Schmiedestücken aus Stahl—Teil 3: Ultraschallprüfung von Schmiedestücken aus ferritischem and martensitischem Stahl (Non-destructive testing of steel forgings—Part 3: Ultrasonic testing of ferritic or martensitic steel forgings), which is hereby incorporated by reference. Suitable testing devices and methods are known for the non-destructive testing of a workpiece by means of ultrasound. General reference is made to the textbook by J. and H. Krautkrämer, Werkstoffprüfung mit Ultraschall, ISBN-13: 978-3-540-15754-0, 5th edition (1986), Springer (Berlin).

These methods are generally based on the reflection of sound on boundary surfaces. The sound source most frequently used is an ultrasonic probe or test probe whose radiation is in the frequency range of 10 kHz to 100 MHz. In the case of the pulse-echo method, the ultrasonic probe does not emit a continuous radiation, but very short sound pulses with a duration of 1 µs and less. The pulse emanating from the transmitter passes through the workpiece to be inspected with the respective speed of sound, and is almost completely reflected at the solid-air boundary surface. The sound probe is most frequently not only able to transmit pulses, but also to convert incoming pulses into electrical measuring signals; it thus also works as a receiver. The time required by the sound pulse to travel from the transmitter through the work piece and back again is measured with an oscilloscope or a computer unit. Given a known speed of sound c in the material, the thickness of a workpiece, for example, can thus be checked. The core of such a probe is at least one ultrasonic transducer, e.g. in the form of a piezo-electric element. Furthermore, it is known, for example from WO 2007/144271, to use a phased array of several, separately controllable ultrasonic transducers that are in a fixed spatial relation for the generation and reception of the ultrasonic pulses.

The transducer(s) are most frequently coupled to the workpiece to be inspected with a matching layer—also referred to as leading body—disposed therebetween and having, for example, a wedge shape and most frequently being made of a thermoplastic synthetic material such as poly(methyl methacrylate) (PMMA). A coupling surface is provided on the leading body via which the sound generated by the ultrasonic transducer(s) can be coupled into the workpiece to be inspected, with the wedge shape causing the sound to enter into the workpiece obliquely. The leading body and the piezoelectric element(s) are generally disposed in a housing which is closed on its one side and which, on its other side, has a coupling aperture through which the ultrasound emitted by the sound coupling surface can exit.

In order to couple the workpiece and the probe, i.e. the leading body, a couplant (e.g. a glue (solution), gel, water or oil) is applied onto the surface of the workpiece to be inspected. The surface to be tested is most frequently passed over with the probe. This can take place manually, mechanically or automatically (for example in production lines). In the latter case, the test piece is often immersed in a suitable liquid (immersion technique) or wetted in a defined manner for the purpose of transmitting the sound signal.

The sound velocity is one of the essential quantities by means of which the exact location of flaws of a workpiece and/or its dimensions are determined. The sound velocity is assumed to be known in most ultrasound methods.

However, it was found that the sound velocity of the thermoplastic material used for the leading body is highly temperature-dependent, at least in comparison with the primarily metallic workpieces that are to be inspected. This problem is already known from DE 3327526 A1. Here, for temperature compensation in a TR probe, the travel time and thus the temperature-dependent sound velocity is determined by means of a test reflector fitted into the leading body in order to compensate travel time deviations.

A change of the sound velocity in the leading body due to a temperature change, for example in a wedge-shaped leading body, can lead to the insonification angle into the workpiece changing, for example, in comparison with the specification on the leading body. This may also lead to errors also in the case of an electronic adjustment of the insonification angle, for example by means of a phased array.

Furthermore, the determination of sound velocities in a workpiece using the back-face echo of the workpiece is known from DE 3441894 A1.

BRIEF SUMMARY

The invention provides an improved pulse-echo method in which the temperature dependence of the sound velocity in the leading body is measured comparatively easily and accurately and, if necessary, compensated in the evaluation of the ultrasound inspection.

In the method for the non-destructive ultrasound inspection, at least one ultrasonic pulse is radiated into a workpiece to be inspected by means of at least one ultrasonic transmitter. The invention is not limited with regard to the workpiece, but generally, it will comprise an acoustically conductive material. The ultrasonic pulse is reflected on boundary surfaces, for example its back face, and discontinuities in the workpiece. The reflected ultrasound is received by means of the at least one ultrasonic receiver and the associated signals are evaluated. The recorded signals are displayed, for example, in a time- or space-dependent representation, for example by an oscilloscope or a computer program product run on a computer with a display device. The space-dependent representation, for example, is linked to the time-dependent representation through the sound velocity. During its propagation from the transmitter to the workpiece and on the way back from the workpiece to the receiver, the ultrasound passes through a, for example wedge-shaped, leading body disposed between the workpiece and the transmitter or receiver.

The method is characterized in that at least one step for determining the sound velocity in the leading body is provided that is precedent, intermediary or subsequent to the above-mentioned inspection of the workpiece, wherein, by means of a phased array comprised of selectively controllable transducers, at least one first transducer acts as a transmitter of at least one ultrasonic pulse, and at least one second transducer acts as a receiver of the ultrasonic pulse, respectively, and the sound velocity in the leading body is determined at least by means of the calculated, shortest sound path of the ultrasound between said transducers. Apart from the shortest distance between the transducers, their measured distance to the coupling surface that is perpendicular to the coupling surface on the workpiece can be used for calculating the sound path.

Several problems can be solved in a simple manner by using a phased array with selectively controllable transducers. By means of selectively using transducers that are spatially as distant from one another as possible as transmitters or receivers, a comparatively long sound path, for example substantially in the direction of the longitudinal direction of the mostly slim leading body, can, on the one hand, be used for determining the sound velocity of the testing sound; the accuracy of the determination of the sound velocity is increased by a sound path that is as long as possible. Therefore, the outermost transducers of the phased array are preferably used in the step for determining the sound velocity, in order to achieve as long a sound path as possible and to increase accuracy.

On the other hand, using a phased array opens up the possibility, by choosing the location and/or by the number of the selectively controlled transducers, of easily adapting the sound emission to the geometry and/or attenuation of the leading body in such a way that the emitted ultrasonic pulse actually reaches a receiver. Preferably, the phased array therefore comprises more than three selectively controllable transducers. Moreover, a test reflector that interferes with the actual ultrasound inspection is advantageously dispensable. In a simple case, the measurement of the temperature-dependent sound velocity can serve for detecting the overheating of the leading wedge.

Preferably, the sound velocity of the leading body determined in the step for determining the sound velocity is used in the evaluation of the signals in the ultrasound inspection of the workpiece. As is described in the introduction, the space-dependent representation is linked to the time-dependent representation through the sound velocity varying with the temperature. Therefore, an accurate, almost simultaneous determination of the sound velocity serves for increasing the accuracy of the ultrasound inspection of the workpiece, for example with regard to its dimensions or the positions of the discontinuities contained therein. It should be clear to the person skilled in the art that he is able to enhance the accuracy of the sound velocity determination in the leading body by repeating the step, by reversal of the sound propagation in the process and/or by using further transducers, i.e. sound paths.

In the step for determining the sound velocity in the leading body, the sound velocity is preferably determined by means of at least one back-face echo of the leading body. On the one hand, a long sound path is thus obtained, on the other hand, it is accomplished that the ultrasound propagation occurring in the process takes place by means of longitudinal waves and not by surface waves, whose sound velocities differ.

Generally, the leading body can have any shape. Depending on the shape of the leading body, the shortest sound path can be calculated geometrically or by numerical simulation ("ray tracing"). For example, at least the distance between the at least two transducers acting as transmitter or receiver is measured and used for the calculation. Preferably, the leading body is a wedge-shaped or has two plane-parallel surfaces. The shortest sound path of the ultrasound can thus be determined by simple geometric calculations during the determination of the sound velocity.

The method is particularly suitable in the case of a leading body made from a thermoplastic synthetic material, in particular from a cross-linked polystyrene copolymer, for example Rexolite®, because this material has a particularly pronounced dependency of the sound velocity on the temperature, for example compared with metals.

According to another preferred embodiment, during the step for the determination of the sound velocity in the leading body, the latter is uncoupled. "Uncoupled" within the sense of the invention is to be understood to mean that it is not coupled to the workpiece to be inspected. For example, it is coupled to air. The ultrasound propagation in the leading body is thus not affected by the coupled workpiece. In particular if a back-face echo is used, the reflectance and thus the accuracy of the step determining the sound velocity is increased by a coupling to air, due to the large change of the acoustic impedance at the transition from the leading body to the ambient air. For this reason, an uncoupled state is to be understood, in principle, as the adjacency of the coupling surface to any medium, wherein the latter has a considerably different acoustic impedance from the material of the leading body, so that, preferably, an internal acoustical total reflection of the testing sound occurs in the leading body.

Furthermore, the method comprises at least one step in which the travel time of the back-face echo of the leading body's coupling surface adjoining, or to be adjoined to, the workpiece is determined for at least one of the transducers acting as a transmitter or receiver. That is, the travel time of the ultrasound is additionally determined which is emitted by the at least one transducer that acts in the previously described step as a transmitter or receiver, is reflected on the back face, i.e. the coupling surface, and is received by the same transducer. A manual measurement of this distance can thus be dispensed with. Moreover, an accurate and current determination can thus take place because the dimensions of the leading body, as a rule, are subject to wear-related changes. For example, in the case of a wedge-shaped leading body, the shortest sound path between the transducers can be determined very accurately by means of the distance between the transducers and two travel time measurements of the back-face echo in which the transducer concerned, respectively, acts as a transmitter and a receiver.

Preferably, the phased array comprises the at least one ultrasonic transmitter which, for the non-destructive ultrasound inspection, emits at least one ultrasonic pulse into the workpiece to be inspected, and the at least one ultrasonic receiver which receives the ultrasonic pulses. In other words, the phased array is used both for the determination of the sound velocity in the leading body as well as for the actual ultrasound inspection of the workpiece. This simplifies the method according to the invention.

In the evaluation in the step for determining the sound velocity in the leading body, the signal of the receiving transducer of the phased array can be triggered to the rising flank or a zero crossing of the pulse echo in order to determine the travel time. Surprisingly, however, it was found that accuracy can be increased in the case of triggering to the pulse peak of the received pulse echo, which is why this process is preferably used. In this case, the evaluation can take place in a control unit (not shown) formed separately from the probe. The digital and optionally analog electronic control system required for controlling the phased array in order to emit ultrasonic pulses can be combined therewith into a joint control and evaluating unit.

In another preferred embodiment of the method according to the invention, a phased array is used for generating the ultrasonic pulses for material inspection. In the process, this is controlled in such a way that the insonification angle into the workpiece is adjusted in a controlled manner. To this end, the sound velocity c in the leading body determined within the context of the method according to the invention is taken into account in the electronic adjustment. This particular process can be implemented, in particular, in the above-mentioned control and evaluation unit.

It is noted that the conclusions can be drawn as to the temperature of the leading body, and thus, indirectly, also as to the temperature of the workpiece, from the sound velocity c in the leading body determined by means of the method according to the invention by means of the connection between the temperature and the sound velocity shown in the table. Optionally, a temperature-related correction of the sound velocity in the workpiece can be determined therefrom, which may, for example, have an influence on the insonification angle resulting in the workpiece in the case of oblique insonification. This can be advantageous, for example, in connection with the so-called DGS method. By way of example, reference is made in this context to the patent applications DE 10 2008 037 173, DE 10 2008 002 445 and DE 10 2008 002 450 by the same applicant, which are connected to the generalizing expansion of the so called DGS method to testing devices with an electronically adjustable insonification angle. The aforementioned patent applications are hereby incorporated by reference into the content of the disclosure of the present application. Method steps of such a correction method suitable therefore also constitute a preferred development of the method according to the invention and can be integrated, in particular, in a control and evaluation unit of the device according to the invention.

The invention moreover relates to a device for carrying out the method in at least one of the above-described advantageous embodiments. The device comprises at least one ultrasonic transmitter for emitting at least one ultrasonic pulse into a workpiece to be inspected, with the ultrasonic pulses being reflected on boundary surfaces in the workpiece. Moreover, at least one ultrasonic receiver for receiving the reflected ultrasound, an evaluation unit for evaluating the associated signals, and a leading body are provided which is disposed between the workpiece and the transmitter such that the ultrasound passes through it. The device is characterized in that the device comprises a phased array of selectively controllable transducers for carrying out the at least one step for determining the sound velocity in the leading body, wherein, respectively, at least one first transducer of the phased array acts as a transmitter of at least one ultrasonic pulse, and at least one second transducer of the phased array acts as a receiver of the ultrasonic pulse, and the sound velocity in the leading body is determined at least by means of a travel time measurement of the ultrasound along the shortest sound path of the ultrasound between said spaced transducers.

As was already explained above, several problems can be solved in a simple manner by using a phased array with selectively controllable transducers. By means of selectively using transducers that are spatially as distant from one another as possible as transmitters or receivers, a comparatively long sound path (for example substantially in the direction of the longitudinal direction of the mostly slim leading body) can, on the one hand, be used for determining the sound velocity of the testing sound in the leading body; the accuracy of the determination of the sound velocity is increased by a sound path that is as long as possible. On the other hand, using a phased array opens up the possibility, by choosing the location and/or by the number of the selectively controlled transducers, of easily adapting the sound emission to the geometry and/or attenuation of the leading body in such a way that the emitted ultrasound actually reaches a receiver. Preferably, the phased array therefore comprises more than two selectively controllable transducers. Moreover, a test reflector that interferes with the actual ultrasound inspection is advantageously dispensable.

BRIEF DESCRIPTION OF THE DRAWING

The invention will be explained below with reference to a schematic illustration, as well as to the associated geometric calculation and to a preferred embodiment, without limiting the invention to what is shown and described.

DETAILED DESCRIPTION

In the preferred embodiment of the method according to the invention, an ultrasound inspection by means of a pulse echo is carried out on a workpiece, which is not shown in FIG. 1, by means of the probe shown in FIG. 1. The phased array 1 of the probe which is also used in the determination of the sound velocity in the leading body 4, as will be described later, is used in this embodiment. The phased array 1 comprises several (in this case 22) selectively controllable sound transducers 2, 3. During the ultrasound inspection, they can be controlled jointly and in phase, but jointly mutually out of phase, selectively in groups etc. The invention is not limited with regard to the process of the ultrasound inspection, and it is the responsibility of the person skilled in the art to select the respectively suitable controlling option. The ultrasound generated by the transducers 2, 3 of the phased array 1 passes through a leading body 4 of thermoplastic material in order to enter the workpiece, which is disposed adjacent to the coupling surface 5 of the wedge-shaped leading body 4, which is hereinafter also referred to as "leading wedge". As was described above, the sound velocity in the leading wedge 4 is generally highly temperature-dependent as compared with the workpiece. As a rule, however, carrying out a separate temperature measurement on the leading body 4 is dispensable since the sound velocity c in the leading body is a direct result of the method according to the invention. In the event it is nevertheless advantageous under certain circumstances to know the absolute value T of the temperature of the leading body in addition to the sound velocity c, the temperature of the leading body can be deduced from tables for the material of the leading body based on the measured sound velocity c.

In order to increase the accuracy of the ultrasound inspection for, if possible, all temperatures, a step for determining the sound velocity in the leading wedge 4 is proposed according to the invention. This step can be carried out before, after or in between the above-described ultrasound inspection and can be repeated several times, if necessary.

In this step, the phased array 1 is also used for ultrasound emission. Moreover, the leading wedge 4 is not coupled with its coupling surface 5 to a workpiece, i.e. it is uncoupled, and the measurement is made, for example, against air. In this embodiment, the step comprises three individual steps. In two steps, the respective back-face echo of the strongly divergent sound beams generated, respectively, by the outermost transducers 2 and 3 is received by them, and the associated travel times $t_1$ and $t_2$ are determined by means of the respective back-face echo. These sub-steps can be offset in time, but can also be carried out simultaneously. It should be noted that the shortest sound paths for the ultrasound are the paths $d_1$ and $d_2$, which correspond to the respective perpendicular distances of the transducers 2, 3 to the coupling surface 5. In a third sub-step, the travel time t of the ultra sound from the transducer 3 as a transmitter to the transducer 2 as a receiver (or vice versa) is measured while a back-face echo is formed. The shortest sound path $e_1+e_2$ of the ultrasound is characterized by the angle of incidence β corresponding to the angle of reflection β at the back-face of the leading body 4 (coupling surface 5).

In the case of a thicker, for example, wedge-shaped leading body, it may be advantageous if the above-described acquisition of the back-face echo on the uncoupled body is not carried out by means of the sound beam of a single transducer of the phased array, but if several (adjacent) transducers of the phased array are combined, for example, on the right edge and on the left edge in order to generate sound beams with a reduced divergence. Such a modified process control is also supposed to be comprised by the method according to the invention.

The sound velocity c in the leading wedge 4 can be determined from the three measured travel times $t$, $t_1$, $t_2$ and the known or previously determined (invariable) distance of the transducers w:

$$c = \frac{w}{\sqrt{t^2 - t_1 t_2}} = w(t^2 - t_1 t_2)^{-\frac{1}{2}}$$

The formula is based on the following geometric calculations:

The distances $d_1$ and $d_2$ can be calculated therefrom as follows:

$$d_1 = \frac{ct_1}{2} \quad d_2 = \frac{ct_2}{2} \tag{1}$$

$e_1$ and $e_2$ can be determined by means of the triangles ΔABC and ΔBCD:

$$e_1 = \frac{d_1}{\sin\beta} \quad e_2 = \frac{d_2}{\sin\beta} \tag{2}$$

The following applies for the sum of $e_1$ and $e_2$:

$$e_1 + e_2 = ct \tag{3}$$

Together with the above equations for $e_1$ and $e_2$, this corresponds to:

$$ct \sin\beta = d_1 + d_2 \tag{4}$$

Converting this, using the equations (1) for $d_1$ and $d_2$, the following is obtained:

$$\sin\beta = \frac{t_1 + t_2}{2t} \tag{5}$$

The following is obtained by means of the law of cosines of the triangle ΔBDE:

$$w^2 = e_1^2 + e_2^2 - 2e_1 e_2 \cos(180° - 2\beta) \tag{6}$$

With $$\cos(180° - 2\beta) = 2\sin^2(\beta) - 1 \tag{7}$$

the use of the equations (2) and (6) yields:

$$w^2 \sin^2(\beta) = d_1^2 + d_2^2 - 2d_1 d_2(\sin^2(\beta) - 1) \tag{8}$$

The equations (1), (5) and (8) yield:

$$w^2 \left(\frac{t_1 + t_2}{2t}\right)^2 = c^2 \left\{ \frac{t_1^2}{4} + \frac{t_2^2}{4} - \frac{t_1 t_2}{2} \left( \left(2\left(\frac{t_1 + t_2}{2t}\right)^2 - 1\right)\right) \right\} \tag{9}$$

Or, correspondingly:

$$c = \frac{w}{\sqrt{t^2 - t_1 t_2}} = w(t^2 - t_1 t_2)^{-\frac{1}{2}}$$

In the illustrated wedge-shaped leading body 4 of the probe, the sound velocity c in the leading body 4 can therefore be determined by measuring the travel times $t$, $t_1$, $t_2$. The sound velocity in the leading body, which has thus been accurately determined and exists in actual fact, is then taken as a basis for the spatially resolving evaluation of the actual ultrasound inspection of the workpiece (e.g. in the determination of the insonification angle and in the workpiece), thus increasing its determination accuracy.

The invention claimed is:

1. Method for non-destructive ultrasound inspection, wherein at least one ultrasonic pulse is radiated by means of at least one ultrasonic transmitter into a workpiece to be inspected and the at least one ultrasonic pulse is reflected on boundary surfaces in the workpiece, a reflected ultrasound is received by means of at least one ultrasonic receiver and a plurality of associated signals are evaluated, and the at least one ultrasonic pulse passes through a leading body which is disposed between the workpiece and the transmitter or receiver, wherein the method comprises at least one step for determining sound velocity in the leading body by means of a phased array comprised of selectively controllable transducers, wherein at least one first transducer of the phased array acts as a transmitter of the at least one ultrasonic pulse, and at least one second transducer of the phased array acts as a receiver of the at least one ultrasonic pulse, respectively, wherein the at least one first transducer of the phased array and the at least one second transducer of the phased array are spaced as distant from one another as possible, the sound velocity in the leading body is determined at least by means of a travel time measurement of the at least one ultrasonic pulse along a shortest sound path of the at least one ultrasonic pulse between the at least one first transducer of the phased array and the at least one second transducer of the phased array, and the sound velocity in the leading body is used in an evaluation of the at least one ultrasonic pulse from the ultrasound inspection of the workpiece.

2. Method according to claim 1, wherein, in the step for determining the sound velocity in the leading body, the sound velocity is determined by means of at least one back-face echo of the leading body.

3. Method according to claim 1, wherein the shortest sound path is calculated geometrically or by numerical simulation.

4. Method according to claim 1, wherein the leading body is wedge-shaped or has two plane-parallel surfaces.

5. Method according to claim 1, wherein the leading body comprises a thermoplastic synthetic material.

6. Method according to claim 1, wherein, in the step for determining the sound velocity in the leading body, the leading body is uncoupled.

7. Method according to claim 2, wherein the method comprises at least one further step in which travel time of the back-face echo of a coupling surface of the leading body adjoining, or to be adjoined to, the workpiece is determined for at least one transducer of the phased array acting as a transmitter or receiver.

8. Method according to claim 1, wherein the phased array comprises the at least one ultrasonic transmitter which, for the non-destructive ultrasound inspection, emits at least one ultrasonic pulse into the workpiece to be inspected, and the at least one ultrasonic receiver which receives the ultrasonic pulses.

9. Method according to claim 1, wherein the phased array comprises more than two selectively controllable transducers.

10. Method according to claim 1, wherein the evaluation in the step for determining the sound velocity is carried out by means of triggering to a pulse peak of a received pulse echo.

11. Device for carrying out the method according to claim 1, comprising at least one ultrasonic transmitter for emitting at least one ultrasonic pulse into a workpiece to be inspected, with the at least one ultrasonic pulse being reflected on boundary surfaces in the workpiece, and at least one ultrasonic receiver for receiving a reflected ultrasound, an evaluation unit for evaluating a plurality of associated signals, and a leading body, which is disposed between the workpiece and the transmitter or receiver such that the at least one ultrasonic pulse passes through the leading body, wherein the device comprises a phased array of selectively controllable transducers for carrying out the at least one step for determining the sound velocity in the leading body, wherein, respectively, at least one first transducer of the phased array acts as a transmitter of at least one ultrasonic pulse, and at least one second transducer of the phased array acts as a receiver of the at least one ultrasonic pulse, and the sound velocity in the leading body is determined at least by means of a travel time measurement of the at least one ultrasonic pulse along a shortest sound path of the ultrasound between the at least one first transducer of the phased array and the at least one second transducer of the phased array.

* * * * *